(12) United States Patent
Panchal et al.

(10) Patent No.: US 11,721,419 B2
(45) Date of Patent: Aug. 8, 2023

(54) APPARATUS FOR FACILITATING SECURE EXCHANGE OF MEDICAL DATA PERTAINING TO A USER, SYSTEM AND METHOD THEREOF

(71) Applicant: S-SQUARE SYSTEMS, LLC, South Barrington, IL (US)

(72) Inventors: Rajendra A. Panchal, Barrington, IL (US); Darshana R. Panchal, Barrington, IL (US); Arun Sobti, Barrington, IL (US)

(73) Assignee: S-SQUARE SYSTEMS, LLC, South Barrington, IL (US)

( * ) Notice: Subject to any disclaimer, the term of this patent is extended or adjusted under 35 U.S.C. 154(b) by 322 days.

(21) Appl. No.: 16/953,928

(22) Filed: Nov. 20, 2020

(65) Prior Publication Data
US 2021/0158921 A1 May 27, 2021

Related U.S. Application Data

(60) Provisional application No. 62/964,705, filed on Jan. 23, 2020, provisional application No. 62/939,166, filed on Nov. 22, 2019.

(51) Int. Cl.
*H04W 12/50* (2021.01)
*H04B 1/38* (2015.01)
(Continued)

(52) U.S. Cl.
CPC ............ *G16H 10/65* (2018.01); *G16H 10/60* (2018.01); *G16H 40/67* (2018.01); *G16H 80/00* (2018.01); *H04N 23/51* (2023.01); *H04N 23/54* (2023.01); *H04N 23/57* (2023.01); *H04N 23/611* (2023.01); *G10L 15/26* (2013.01)

(58) Field of Classification Search
CPC ........ G16H 10/65; G16H 10/60; G16H 40/67; G16H 80/00; H04N 23/51; H04N 23/54; H04N 23/57; H04N 23/611; H04N 23/695; H04N 23/50; G10L 15/26; H04W 12/06;
(Continued)

(56) References Cited

U.S. PATENT DOCUMENTS 9,832,019 B2 * 11/2017 Choi ........................ G06F 21/33
2004/0125938 A1 * 7/2004 Turcan .................... H04M 3/54
379/265.02

(Continued)

*Primary Examiner* — Andrew Wendell
(74) *Attorney, Agent, or Firm* — D'Ambrosio & Menon, PLLC; Usha Menon

(57) ABSTRACT

The present disclosure provides an apparatus and system for remote health applications that are compliant with Health Insurance Portability and Accountability Act (HIPAA). The apparatus includes an adjustable stand to accommodate a digital communications device such as a tablet or smart phone. The dock is further operatively coupled to one or more sensors attached to a patient to monitor health parameters of the patient. A similar dock s provided with a medical care provider. The docks are registered, and as authentication, any exchange of information can occur only between registered docks. A simultaneous audio-video communication between the patient and the medical care provider and exchange medical and non-medical data that is governed by HIPAA can occur between the registered docks.

20 Claims, 13 Drawing Sheets

(51) Int. Cl.
*G16H 10/65* (2018.01)
*G16H 80/00* (2018.01)
*G16H 40/67* (2018.01)
*H04N 23/51* (2023.01)
*H04N 23/54* (2023.01)
*H04N 23/57* (2023.01)
*H04N 23/611* (2023.01)
*G16H 10/60* (2018.01)
*G10L 15/26* (2006.01)

(58) Field of Classification Search
CPC ........ H04W 12/30; H04W 12/50; H04B 1/38; H04B 1/3827
See application file for complete search history.

(56) References Cited

U.S. PATENT DOCUMENTS

| | | | |
|---|---|---|---|
| 2008/0021834 A1* | 1/2008 | Holla | H04L 63/0428 705/51 |
| 2010/0250957 A1* | 9/2010 | Cuppett | G06F 21/41 713/186 |
| 2011/0131237 A1* | 6/2011 | Macaluso | G06F 16/27 707/769 |
| 2017/0094090 A1* | 3/2017 | Sato | H03K 19/177 |
| 2021/0065917 A1* | 3/2021 | Masroor | G16H 80/00 |
| 2021/0073855 A1* | 3/2021 | Francia | G06Q 30/0275 |
| 2022/0116357 A1* | 4/2022 | Rudolph | H04L 63/1416 |

\* cited by examiner

APPARATUS FOR FACILITATING SECURE EXCHANGE OF MEDICAL DATA PERTAINING TO A USER, SYSTEM AND METHOD THEREOF

CROSS REFERENCE TO RELATED APPLICATION(S)

This application claiming priority to U.S. provisional application Nos. 62/939,166 and 62/964,705 filed on Nov. 22, 2019 and Jan. 23, 2020. The above identified applications are incorporated by reference.

TECHNICAL FIELD

The present disclosure relates generally to the field of telemedicine or remote health applications. In particular, the present disclosure relates to a system for secure exchange of health data between a patient and a medical care provider, the exchange adding a channel that is secure and controls access to authenticated members besides being compliant to the Health Insurance Portability and Accountability Act (HIPAA).

BACKGROUND

Background description includes information that may be useful in understanding the present invention. It is not an admission that any of the information provided herein is prior art or relevant to the presently claimed invention, or that any publication specifically or implicitly referenced is prior art.

The Health Insurance Portability and Accountability Act (HIPAA), 1966 is a legislation that provides data protection in the health industry between a patient and a medical care provider. The regulations as provided by HIPAA govern the protocols to be established for exchange of medical and non-medical data pertaining to the patient such that the exchange is secure and is protected against fraudulent acquisition. An important protocol for exchange of electronic data is authentication of the identity of the patient and the medical care provider to initiate the exchange.

Most devices designed for remote health applications are either bulky owing to the number of components required to make them HIPAA compliant or, they have achieved this compliance for video conferencing only through specialised applications on the mobile without being able to simultaneously deliver medical parameters from the remote patient's bedside.

The current state-of-the-art allows medical parameters to be entered either after the video conference. This form of a remote medical visit while acceptable under HIPAA standards is advised against by health medical care providers. Caregivers prefer to be in-charge of administering the vital sign devices similar to as they are accustomed to do in the doctor's office for their own supervised quality assurance of the measurements. While every doctor's preference may differ over time on a case by case basis and experience of the patient. The remote medical visit should ideally provide any required medical parameters in a caregiver administered 'supervised' manner, i.e., all medical measurements should either be conducted in view of a local nurse at the patient's bedside, or by a remote nurse or doctor. This latter requirement of a remote nurse or doctor administering and observing the actual taking of measurements (to ensure that they are taken correctly) can, of course, be performed through elaborate apparatuses that treat the medical measurement system like the dedicated systems built singularly for this by remote applications solutions companies. Such systems are typically very expensive, and this limits the availability of such systems only to a small section of peoples who can afford them.

Simple hand-held devices such as tablets and smart phones, which are enabled with audio-video communications applications would make a viable solution to the above-stated problem. The audio-video communications applications such as Facetime, Skype, Google duo, WhatsApp etc offer secure and encrypted channels of communication but the consumer versions do not provide the necessary authentication requirements for HIPAA.

There is, therefore, a requirement in the art for a remote health applications system that has a small form factor, that is easily accessible and that complies with HIPAA standards. Further, the health applications system can use available hand-held devices such as smart phones and tablets together with other medical devices and environmental sensors to monitor activities of daily life behaviours.

OBJECTS OF THE DISCLOSURE

A general object of the present disclosure is to provide an apparatus for remote health applications that is compliant to the Health Insurance Portability and Accountability Act (HIPAA).

Another object of the present disclosure is to provide an apparatus for remote health applications that can interface with available mobile devices.

Another object of the present disclosure is to provide a system for remote health applications that allows for remote diagnosis and remote prescriptions.

Another object of the present disclosure is to provide a system that provides remote monitoring of health of patients and allows alerts to be raised remotely.

SUMMARY

The present disclosure relates generally to the field of telemedicine or remote health applications. In particular, the present disclosure relates to a system for secure exchange of health data between a patient and a medical care provider, the exchange adding a channel that is secure and controls access to authenticated members besides being compliant to the Health Insurance Portability and Accountability Act (HIPAA).

The present disclosure provides an apparatus for facilitating exchange of medical data pertaining to a user. The apparatus includes: one or more processors operatively coupled with a memory, the memory storing instructions executable by the one or more processors to: receive, from the user of the apparatus, a first data packet pertaining to identity of the user; receive, from a server operatively coupled to the apparatus, a second data packet pertaining to identities of registered users of the apparatus; compare the received first data packet and the received second data packet. The one or more processors are configured to generate a first signal on positive match of the identity of the user of apparatus with at least one of the identities of registered users of the apparatus, the first signal indicative of communications being allowed between the apparatus and the server. The apparatus includes: a first transceiver configured for communications between the apparatus and the server, operable by the one or more processors, on receipt of the first signal, for exchange of data packets of a first kind, and a second transceiver configured for communications between the apparatus and the server, operable by the one or more processors, on receipt of the first signal for exchange of data packets of a second kind.

In an embodiment, the apparatus is configured to register a user to itself on initialisation of the apparatus, wherein the one or more processors are configured to: operatively couple, upon initialisation of the apparatus, with the server; receive, from an initially unregistered user, a request for registration of the apparatus, the request comprising identity attributes of the user, identity attributes of the apparatus and purpose of use of apparatus; receive, from the initially unregistered user, an address of the user for communication of information from the server to the user; request generation of a registration data packet at the server, comprising a registration parameter; request transmission of the registration packet from the server to the address of the user; request the initially unregistered user to input the registration parameter value into the apparatus; and compare the input parameter value with the parameter value of the generated registration data packet. The one or more processors, upon positive match of the input parameter value and the parameter value of the registration data packet, are configured to register the initially unregistered user as a newly registered user of the apparatus; and transmit information pertaining to the newly registered user of the apparatus to the server.

In another embodiment, the apparatus can be operatively coupled with one or more input devices, the input devices configured for exchange of information pertaining to health attributes of the user of the device, wherein the input devices can be any or a combination of camera, microphone, implanted sensors and explanted sensors, and wherein the apparatus can be operatively coupled to the input devices by any or a combination of wired and wireless means.

In another embodiment, the apparatus can include one or more one or more ports adapted for wired coupling between the apparatus and the input devices.

In another embodiment, the apparatus can be provided with a battery adapted to power the apparatus.

In another embodiment, the apparatus can be provided with an interface device operatively coupled to it, and wherein the one or more processors of the apparatus can be configured to operate the interface device to facilitate communications between the user and the apparatus.

In an embodiment, the apparatus can include a movable receptacle fixed at a top surface of the apparatus, the receptacle adapted to hold, rotate and tilt the interface device within a pre-defined range.

In another embodiment, the apparatus can be operable in any or a combination of tilt mode and pan mode; wherein the tilt mode facilitates tilting of the interface device in order to track the user; and the pan mode facilitates panning, through the interface device, to obtain a clear view of the user.

In one embodiment, the apparatus can facilitate a user to select, through any of an input device and the interface device, any or a combination of the tilt mode and pan mode, to operate the interface device.

In other embodiment, the apparatus can include implanted sensors configured to sense motion of the user, and wherein in response to the sensed motion, any or a combination of the tilt mode and pan mode is automatically selected.

In another embodiment, the apparatus can be provided with an interactive voice assistant to facilitate communications between the apparatus and the user through an interface device of the user.

In another embodiment, the data packets of the first kind can pertain to information pertaining to the user that is not protected by a security protocol.

In another embodiment, the data packets of the second kind can pertain to information pertaining to the user that is protected by security protocol.

In an exemplary embodiment, the security protocol can be Health Insurance Portability and Accountability Act (HIPAA).

In one exemplary embodiment, the apparatus can be reduced to provide necessary capabilities and functionalities in a form-factor conducive to be placed near a tabletop or a wall mounted TV or on a bedside nightstand or a family room side table or similar settings.

In another exemplary embodiment, the apparatus can be further reduced to provide necessary capabilities and functionalities in a form-factor conducive to be directly plugged on to an open port of a tabletop or a wall mounted TV. Similarly, the apparatus can be reduced to provide necessary capabilities and functionalities in a form-factor conducive to be placed and connected to another user appliance or enclosure suitable for the user's convenience for the target application.

In an aspect, the present disclosure provides a method to operate an apparatus for facilitating exchange of medical data pertaining to a user. The method includes: receiving, at a processor configured on the apparatus from the user of the apparatus, a first data packet pertaining to identity of the user; receiving, at the processor from a server operatively coupled to the apparatus, a second data packet pertaining to identities of registered users of the apparatus; comparing, at the processor, the received first data packet and the received second data packet; and generating, at the processor, a first signal on positive match of the identity of the user of apparatus with at least one of the identities of registered users of the apparatus, the first signal indicative of communications being allowed between the apparatus and the server. On generation of the first signal, a first transceiver provided on the apparatus and configured for communications between the apparatus and the server is operable by the processor for exchange of data packets of a first kind, and, on generation of the first signal, a second transceiver provided on the apparatus and configured for communications between the apparatus and the server is operable by the processor for exchange of data packets of a second kind.

In another aspect, the present disclosure provides a system for facilitating exchange of medical data pertaining to a user. The system includes: a first apparatus for remote health monitoring registered to the user; a second apparatus for remote health monitoring registered to a medical care provider; and a server operatively coupled with the first apparatus and the second apparatus, comprising one or more processors operatively coupled with a memory, the memory storing instructions executable by the one or more processors to: receive, from the first apparatus, a third data packet pertaining to a request for exchange of data packets with the medical care provider, wherein the first data packet comprises an identification attribute of the user and the first apparatus; receive, from a second apparatus for remote health application, a fourth data packet pertaining to identity of registered users allowed to communicate with the medical care provider; compare the received third data packet and the fourth data packet. The one or more processors is configured to generate a second signal on positive match of the identity of the user with at least one of the identities of registered users allowed to communicate with the medical care provider, the second signal indicative of communications being allowed between the user and the medical care provider. The one or more processors are configured to allow exchange of data packets of a first kind between a first transceiver provided on each of the first apparatus and the second apparatus, and the one or more processors are configured to allow exchange of data packets of a second kind between a second transceiver provided on each of the first apparatus and the second apparatus.

In an embodiment, the server is configured to register a user to an apparatus for remote health applications on initialisation of the apparatus, wherein the one or more processors are configured to: receive, from an initially unregistered user, a request for registration of the apparatus to the user, the request comprising identity attributes of the user, identity attributes of the apparatus and purpose of use of apparatus by the user; receive, from the initially unregistered user, an address of the user for communication of information from the server to the user; generate a registration data packet comprising a registration parameter; transmit the registration packet to the address of the user; request, at the apparatus, the initially unregistered user to input the registration parameter value into the apparatus; and compare the input parameter value with the parameter value of the generated registration data packet. The one or more processors, upon positive match of the input parameter value and the parameter value of the registration data packet, are configured to register the initially unregistered user as a newly registered user of the apparatus.

In an embodiment, the server can be operatively coupled to any or both of the first apparatus and the second apparatus through a mobile computing device operatively coupled correspondingly with the first apparatus and the second apparatus.

In another embodiment, the data packets of the first kind can pertain to information pertaining to the user that is not protected by a security protocol.

In another embodiment, the data packets of the second kind can pertain to information pertaining to the user that is protected by security protocol.

In an exemplary embodiment, the security protocol is Health Insurance Portability and Accountability Act (HIPAA).

In an aspect, the present disclosure provides a method for facilitating exchange of medical data pertaining to a user. The method includes: receiving, at a central computing device, from a first apparatus for remote health applications registered to the user, a third data packet pertaining to a request for exchange of data packets with the medical care provider, wherein the first data packet comprises an identification attribute of the user and the first apparatus; receiving, at the central computing device, from a second apparatus for remote health application registered to a medical care provider, a fourth data packet pertaining to identity of registered users allowed to communicate with the medical care provider; comparing, at the central computing device, the received third data packet and the fourth data packet; generating, at the central computing device, a second signal on positive match of the identity of the user with at least one of the identities of registered users allowed to communicate with the medical care provider, the second signal indicative of communications being allowed between the user and the medical care provider. On generation of the second signal, the central computing device is configured to allow exchange of data packets of a first kind between a first transceiver provided on each of the first apparatus and the second apparatus, and on generation of the second signal, the central computing device is configured to allow exchange of data packets of a second kind between a second transceiver provided on each of the first apparatus and the second apparatus.

Various objects, features, aspects, and advantages of the inventive subject matter will become more apparent from the following detailed description of preferred embodiments, along with the accompanying drawing figures in which like numerals represent like components.

BRIEF DESCRIPTION OF DRAWINGS

The accompanying drawings are included to provide a further understanding of the present disclosure and are incorporated in and constitute a part of this specification. The drawings illustrate exemplary embodiments of the present invention and, together with the description, serve to explain the principles of the present disclosure.

DETAILED DESCRIPTION

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

In an aspect, the present disclosure provides an apparatus and system for remote health applications that are compliant with Health Insurance Portability and Accountability Act (HIPAA). The apparatus comprises a dock 100 configured with an adjustable stand to accommodate a digital communications device such as a tablet or smart phone. The dock 100 is further operatively coupled to one or more sensors attached to a patient to monitor health parameters of the patient.

In another aspect, the connected interface device is operatively coupled with one or more sensors attached to a patient to monitor health parameters of the patient. Thus, the present disclosure provides a combined apparatus with the connected device, which may be configured with any combination of sensors. The sensors can be either attached with the dock 100, the connected interface device or both. A similar dock 100 is provisioned, configured, and provided with a medical care provider.

In another aspect, the docks are registered, and for security, any exchange of information can occur only between registered docks. A simultaneous audio-video communication between the patient and the medical care provider and exchange of medical and non-medical details such as health parameters, payment details, insurance etc. that is governed by HIPAA can occur between the registered docks. The dock 100 enables the use of any available digital communications device to be used for remote health applications while complying with HIPAA guidelines.

Figure 1A:
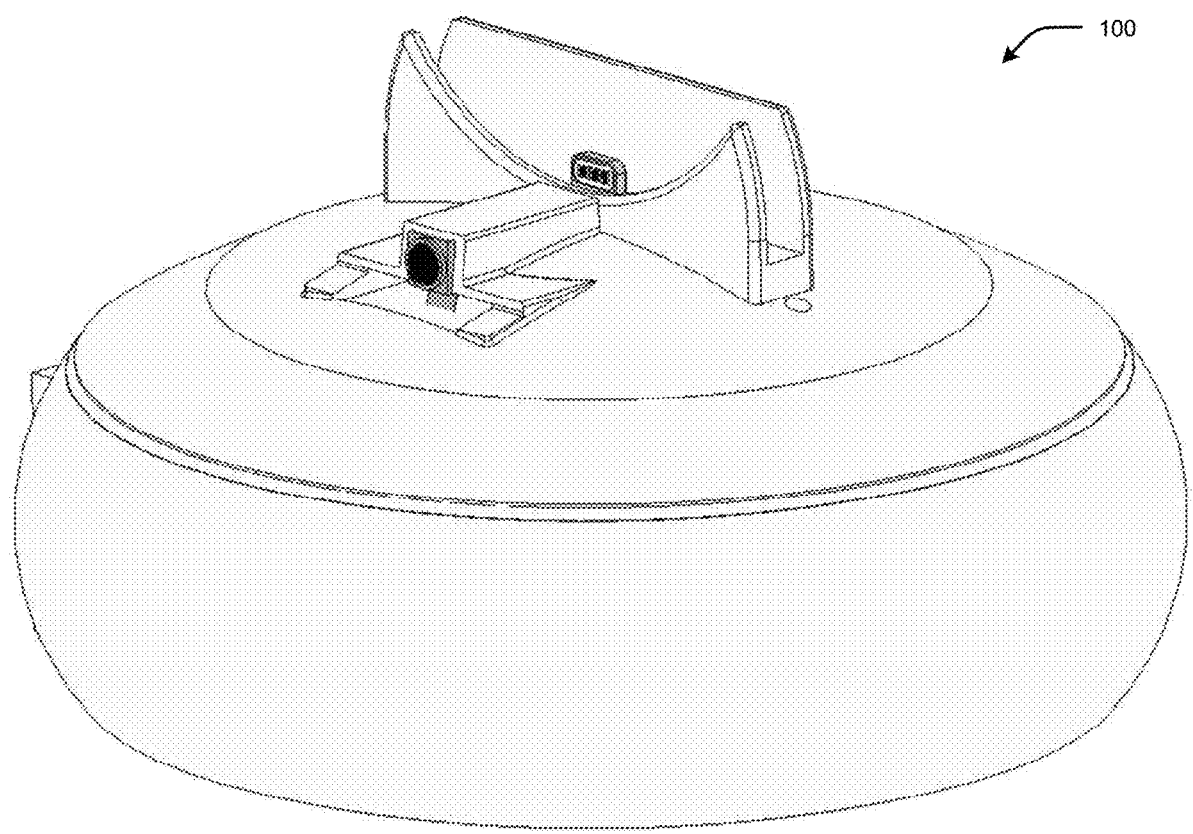
FIGS. 1A and 1B illustrate exemplary representations of an apparatus for remote health applications, and the apparatus for remote health applications along with a dock interface device respectively, in accordance with an embodiment of the present disclosure.
Figure 1B:
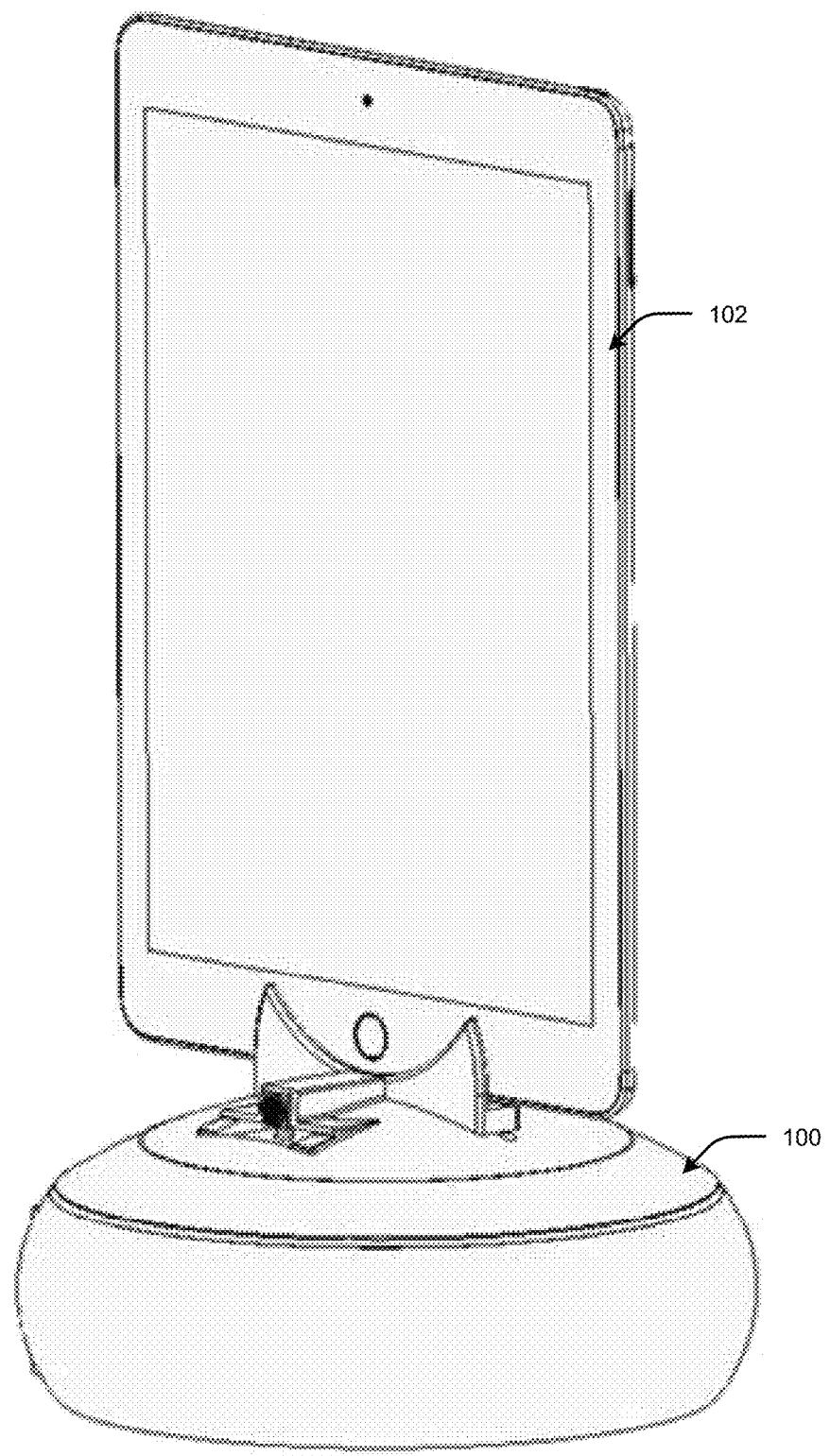

FIGS. 1A and 1B illustrate exemplary representations of an apparatus for remote health applications, and the apparatus for remote health applications along with a connected interface device respectively, in accordance with an embodiment of the present disclosure.

In an embodiment, the apparatus 100 (herein, also referred to as "dock 100") can be dock 100 capable of being operatively coupled to an interface device 102 for remote health applications. The digital interface device 102 can be any device capable of audio-video interfacing such as tablet, smart phone, laptop etc. The dock 100 can include a movable receptacle 104 (interchangeably, referred to as stand 104) to accommodate interface devices 102. In an exemplary embodiment, the receptacle fixed at a top surface of the dock 100, where the receptacle is adapted to hold, rotate and tilt the interface device 102 within a pre-defined range. In another embodiment, the dock 100 can also be operatively coupled to other input means such as keyboard, mouse etc. The input means can also include a touch-enabled screen on the interface device 102 or on the dock 100.

In another embodiment, the input means can include a voice assistant (VA). The dock 100 can be configured with the VA that can be customised for telehealth applications and that can be personalised for a patient or a medical care provider.

In another embodiment, the dock 100 can include an application that is executable by the interface device 102, which can be configured with the VA that can be customised for telehealth applications and that can be personalised for the patient or the medical care provider.

In another embodiment, the input means can also include a camera, which can be provided with an adjustable pan, autofocus/zoom and tilt functionality for the host dock 100. In another embodiment, the application executable by the interface device 102 can include subroutines executable to operate camera of the interface device 102.

Generally, most smart devices available in the art are provided with a VA. However, the extent to which the VA can be customised and personalised is limited by restrictions placed on them by their respective manufacturers.

For collaborative applications such as telehealth, higher order of personalisation is desired to facilitate broader use-cases such as, VA-to-VA collaborations, either locally or remotely. For personalisation, within a given platform ecosystem, across platform ecosystems of the collaborating systems or both, a higher order of personalisation is desired. The application provided with the dock 100 can include provisions for customisation of the VA associated either with the dock 100 or with the interface device 102 that is operatively coupled with the dock 100.

Figure 1C:
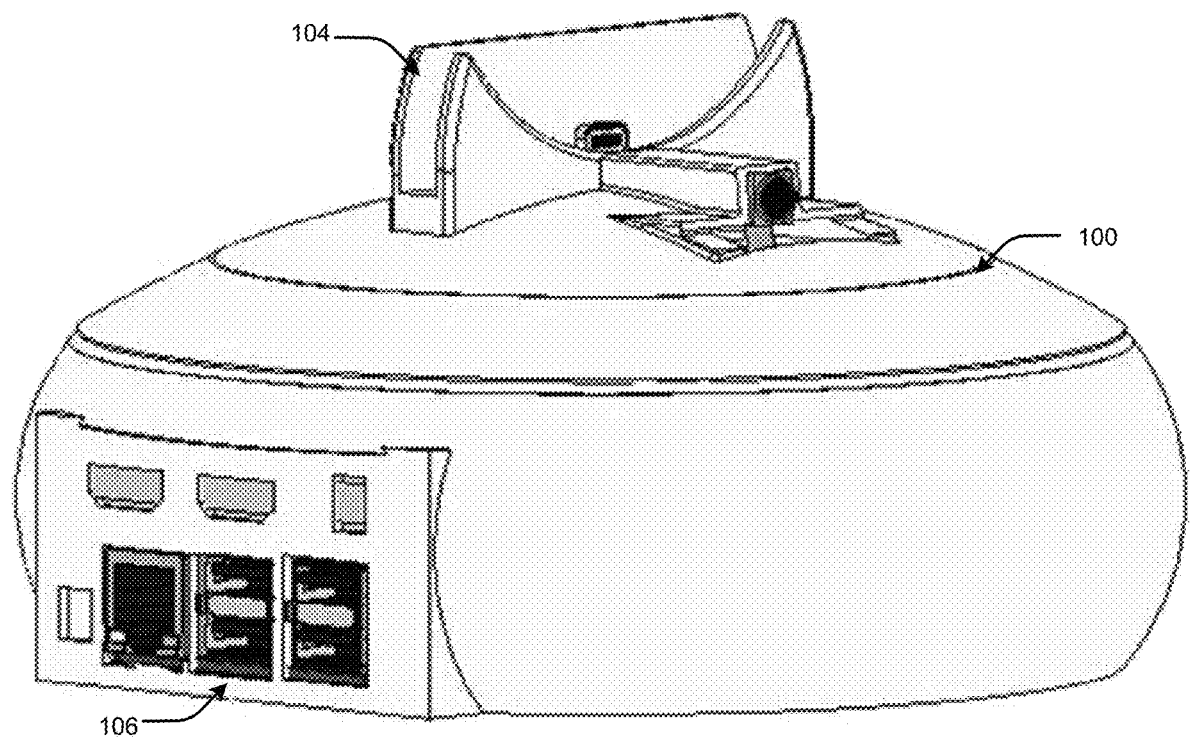
FIG. 1C illustrates an exemplary representation of one or more ports for data transfer provided the proposed apparatus for remote health applications, in accordance with an embodiment of the present disclosure.

In another embodiment, the dock 100 can include a plurality of ports 106 with pins of different configurations to interface with external devices, as illustrated in FIG. 1C. The dock 100 can also be enabled with wireless technologies to enable operative coupling to external devices. The external devices can include a plurality of health sensors, input devices such as keyboards, mouse, scanner, biometric device, microphone etc., output devices such as display, speakers, indicator lamps etc.

In another embodiment, the dock 100 can be powered either through an electric supply or through a battery provided within the dock 100. The dock 100 can be configured with a charging port which receives input power to power the dock 100, to charge the battery or a combination of both.

In another embodiment, the dock 100 can be provided with the stand 104 to accommodate interface devices such as a tablet or a smart phone. The stand 104 can be adjustable in order that the tilt and orientation of the interface device 102 can be adjusted.

In an embodiment, the dock 100 can be operable in any or a combination of tilt mode and pan mode; wherein the tilt mode facilitates tilting of the interface device 102 in order to track the user; and the pan mode facilitates panning, through the interface device 102, to obtain a clear view of the user. In one embodiment, the apparatus can facilitate the user to select, through any of an input device and the interface device, any or a combination of the tilt mode and pan mode, to operate the interface device 102. In other embodiment, the apparatus can include implanted sensors configured to sense motion of the user, and wherein in response to the sensed motion, any or a combination of the tilt mode and pan mode is automatically selected.

In an embodiment, the pan, autofocus/zoom, and tilt orientation can be instrumented leveraging the camera of the connected interface device or that of the dock 100 itself in order to track motion and keep the patient in view. The stand can be configured to automatically tilt or change its orientation to track and locate the patient in the view of the camera, where the pan and tilt functionality can be realised by two or more servo motors installed on the dock 100, and the autofocus/zoom can be realised by the dock 100 by controlling motor of the dock camera itself. When the servo motors rotate in the same direction, tilting functionality is realised, and when they rotate in opposite directions, panning functionality is realised. The dock 100, based on requirement, can switch from tilt to pan functionality and vice-versa.

In another embodiment, the interface device 102 can further be operatively coupled to the dock 100 through a port. Any or both of microphone and speaker can be included in the dock 100, operatively coupled to the interface device 102. In another exemplary embodiment, the dock 100 can be configured with a charging outlet to charge the interface device 102 as it is being held in the stand.

In another exemplary embodiment, the dock 100 can include wireless connectivity technologies such as Wi-Fi, radio, Bluetooth, mobile internet connectivity etc. through which it can receive and transmit data. The dock 100 can be operatively coupled to the external devices through any of the aforementioned wireless communication technologies.

In an exemplary implementation, the dock 100 can be integrated with a system for remote health applications such as remote doctor/patient consultation and remote patient monitoring with real-time vital parameters. The monitoring of the parameters can be administered by the caregiver or patient through outbound connectivity initiation, or automatically through inbound connectivity initiation as configurable according to the caregiver preferences and/or the nature and/or the FDA classification of the external device.

In one exemplary embodiment, size of the apparatus can be reduced to provide necessary capabilities and functionalities in a form-factor conducive to be placed near a tabletop or a wall mounted TV or on a bedside nightstand or a family room side table or similar settings.

In another exemplary embodiment, size of the apparatus can be further reduced to provide necessary capabilities and functionalities in a form-factor conducive to be directly plugged on to an open port of a tabletop or a wall mounted TV. Similarly, the apparatus can be reduced to provide necessary capabilities and functionalities in a form-factor conducive to be placed and connected to another user appliance or enclosure suitable for the user's convenience for the target application.

Figure 2A:
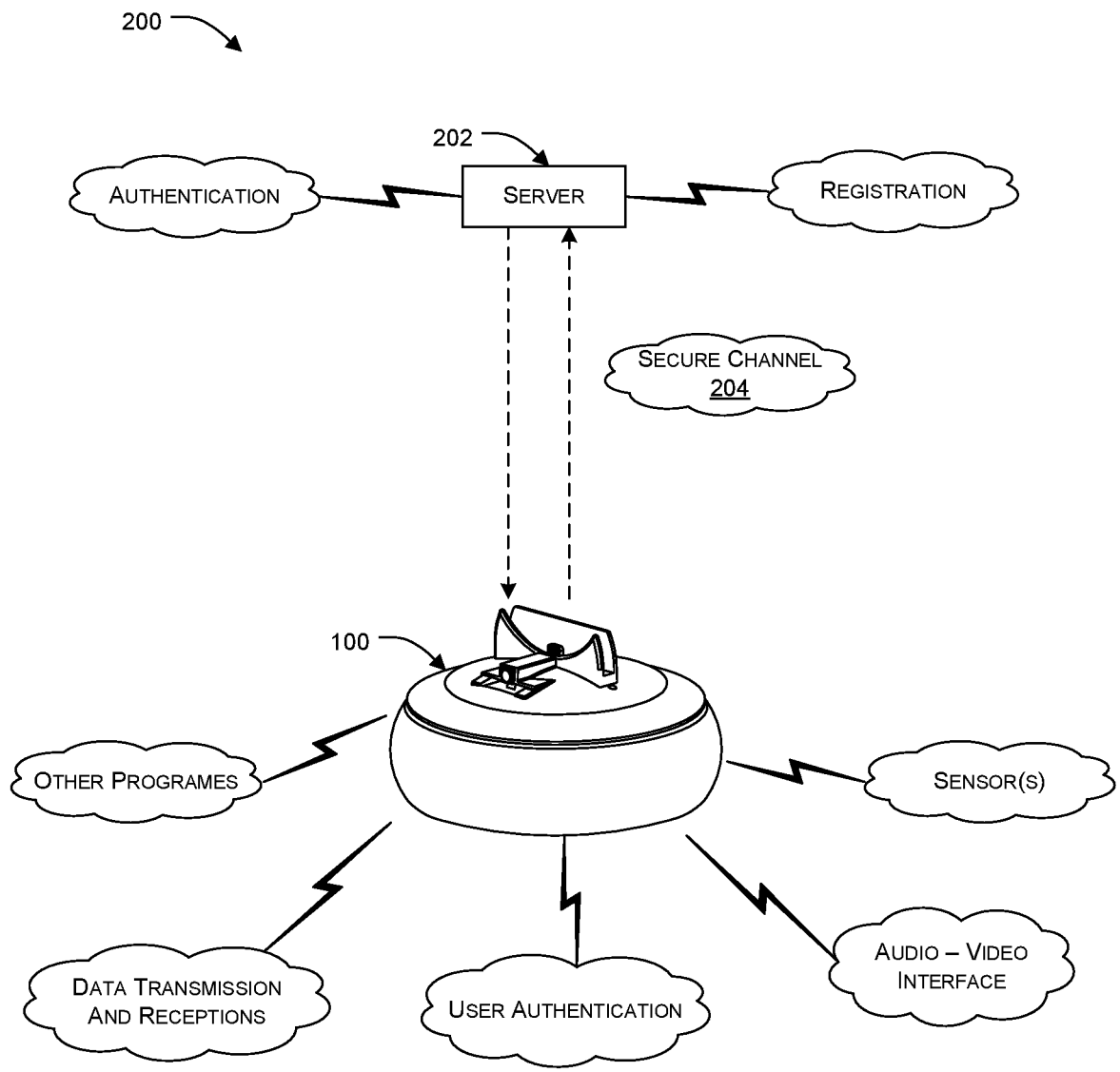
FIG. 2A illustrates an exemplary top-level schematic representation of a system for remote health applications, in accordance with an embodiment of the present disclosure.

FIG. 2A illustrates an exemplary top-level schematic architecture of a system for remote health applications, in accordance with an embodiment of the present disclosure.

In an embodiment, the system 200 can be integrated with the dock 100 of the present disclosure to provide remote health applications. The dock 100 can include one or more processors operatively coupled with a memory, the memory storing instructions to enable remote health applications, which can be executable by the one or more processors.

In another embodiment, the dock 100 can be operatively coupled to a server 202. The dock 100 can be configured to receive updates from external devices pertaining to health applications, that can then be transmitted to the server 202. Communications between the server 202 and the dock 100 can be through secure channels 204. In another embodiment, the server 202 can be further operatively coupled to other docks 100.

In another embodiment, the system 200 is configured such that communication between the server 202 and the dock 100 through the secure channel 204 is possible only for a registered user of the dock 100, and further, communication is possible on authentication of the registered user of the dock 100. Registration and authentication details are stored in the server 202.

Figure 2B:
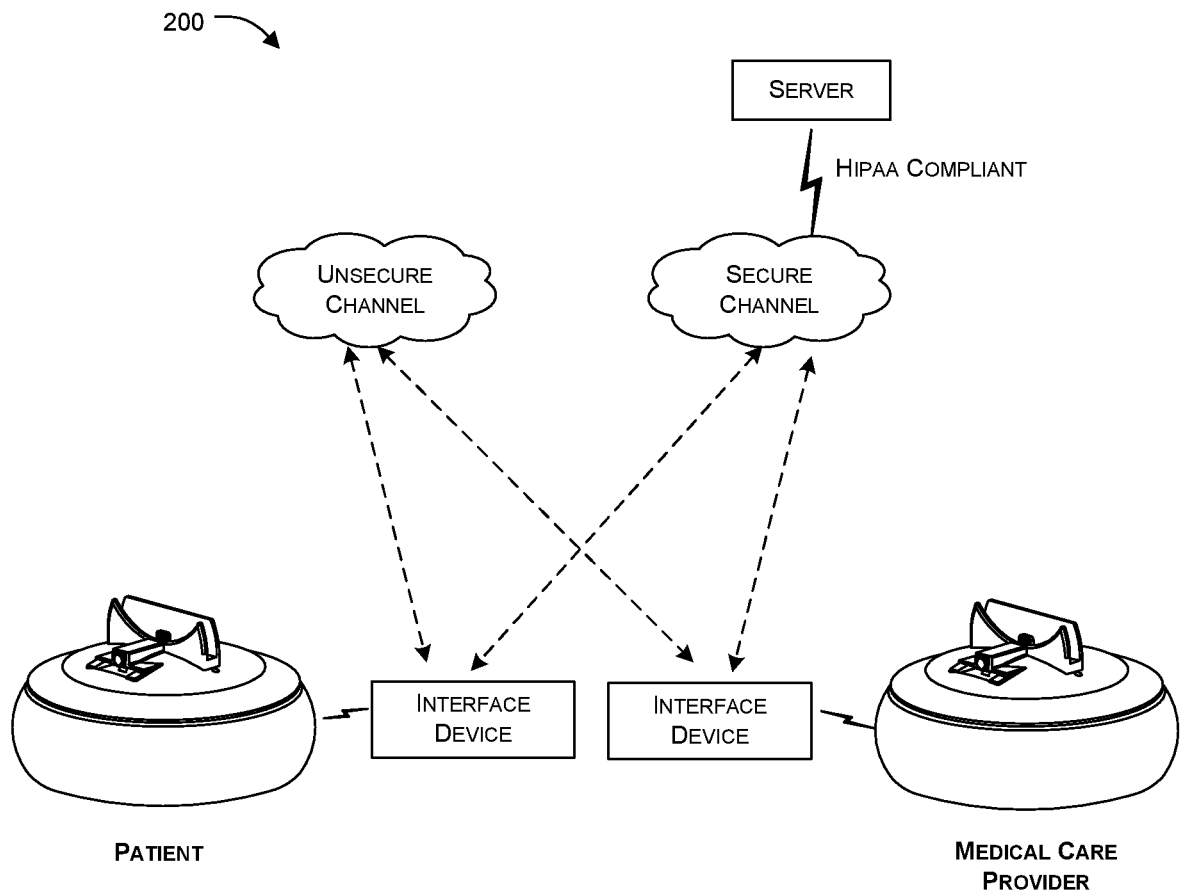
FIGS. 2B and 2C illustrate exemplary architectures for remote health applications using the proposed dock for remote health applications, in accordance with an embodiment of the present disclosure.
Figure 2C:
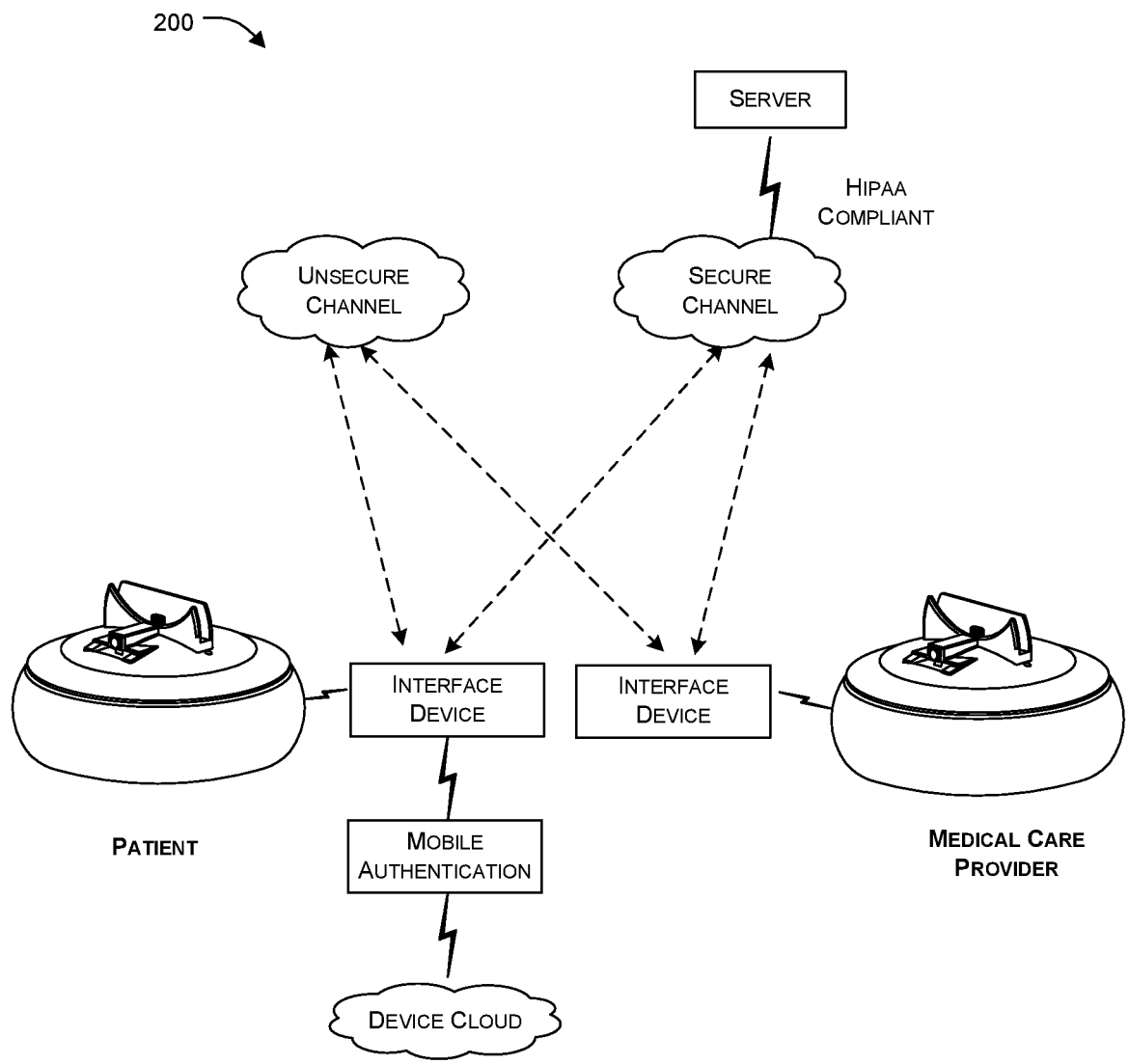

FIGS. 2B and 2C illustrate exemplary representations of communication between a patient and a medical care provider using the proposed dock 100, in accordance with an embodiment of the present disclosure.

In another embodiment, each dock 100 can be registered with the server by means of a unique ID. The registration can further be used as an authentication means required for any of one or a combination of transfer of data between the dock 100 and the server, and transfer of data between the server and the external devices.

In an embodiment, the system is configured to enable a patient to communicate with a medical care provider via the interface device. The interface device can be any touch-enabled device available in the art equipped with any available operating system. The communication means can be any as provided by the interface device.

In another embodiment, dock 100 can be operatively coupled to a plurality of sensors configured to measure different parameters of the patient pertaining to health of the patient and further can be operatively coupled to a plurality of environmental sensors to monitor activities of daily life behaviours of the patient. The parameters can be stored either locally on a memory provided in the dock 100, in the server, or a combination thereof.

In another embodiment, dock 100 connected interface device can be operatively coupled to a plurality of sensors configured to measure different parameters of the patient pertaining to health of the patient and further can be operatively coupled to a plurality of environmental sensors to monitor activities of daily life behaviours of the patient. The parameters can be stored either locally on a memory provided in the dock 100, in the server, or a combination thereof.

In another embodiment, the system is configured for communications using two or more channels. A first channel can allow audio-video communication between the medical care provider and the patient. A second channel can allow exchange of data that is construed to be confidential between the patient and the medical care provider. The confidential information can include, data from the plurality of sensors, non-medical data pertaining to the patient such as insurance details etc. In an exemplary embodiment, the second channel is used for exchange of data that is regulated by an established protocol such as Health Insurance Portability and Accountability Act (HIPAA).

In another embodiment, the system is configured to use both channels simultaneously to exchange data between the patient and the medical care provider. However, exchange is possible only on positive authentication.

In another embodiment, a first step in authentication can be a successful log-in initiated by the patient and the medical care provider, the successful log-in being confirmed at the server. The log-in can be initiated through an application installed on the interface device provided with the patient and the medical care provider. In an embodiment, the log-in can occur at a portal running on the server. In an exemplary embodiment, the portal can be "PodNET".

In another embodiment, the provisioning of the dock 100 ("HealthPOD") for a user can occur on a portal (such as PodNET) using mobile verification means. For instance, on purchase of a HealthPOD device by a user, the user can be directed, on start-up of the HealthPOD, to the PodNET for provisioning of the HealthPOD. The provisioning can include input of user details and a user need for the HealthPOD (such as whether the HealthPOD is to be used by a doctor or a patient). Upon input of the details, a verification means (such as a one-time password or a QR code) can be communicated to the user via a registered landline telephone number, a registered mobile number, an email ID, a dedicated application for receiving the verification means or by a combination thereof. Further, the registered mobile number or the registered landline number can be used to verify the location of the user and the HealthPOD. The user can allow the verification means to be scanned by the camera on HealthPOD, whereupon the HealthPOD is provisioned based on the details input by the user at the portal.

In another embodiment, the VA on the HealthPOD can be activated on start-up and can request and guide the user to for provisioning of the HealthPOD.

In another embodiment, the VA of the HealthPOD can be activated on start-up and can request the user to provide a verification means for provisioning of the HealthPOD. This can occur in an instance when a HealthPOD device is obtained by the user after the user details have already been updated on the PodNET, such as when the user is obtaining a HealthPOD for a first time, a replacement HealthPOD or an additional HealthPOD. On start-up, the VA is configured to request for verification means. The verification means can then be scanned by the camera on HealthPOD, whereupon the HealthPOD is provisioned based on the details input by the user at the portal.

In another embodiment, a second step in authentication can be by registration of docks. The channels of communication can only be used only between docks that are registered. The registration of the docks is confirmed by the system at the server end of the system.

In another embodiment, the second step in authentication can be performed between any of two registered docks, a registered dock 100 and an interface device operatively coupled to a registered dock 100 and between two interface devices, each interface device operatively coupled to a registered dock 100.

In another embodiment, above first step and the second step can be instrumented by using a mobile application on the interface device when the user docks the interface device. Upon physical docking, the interface device, and the dock 100 can be enabled to recognise the type of interface device being that it is being connected with and can invoke the corresponding mobile application on the interface device automatically. Alternatively, the user can manually invoke the mobile application after the physical docking. Upon being invoked, the mobile application can automatically perform the authentication of the interface device as well as the host dock 100 with the server. Upon successful bonded-authentication, the server and the host dock 100 can perform provisioning either from over-the-air downloaded by the interface device or by the dock 100 retrieving the provisioning directly from the server now that the server knows the identity of the dock 100 bonded-authentication and registration.

It should be appreciated that that future smart device can be connected wirelessly.

In another embodiment, either upon power-on or upon request, the VA on the dock 100, can provide a list of smart devices it sees in the Wi-Fi network and allow the user to select a preferred device to pair-authenticate with the dock 100. The user can then select the preferred device and manually invoke the Mobile App to perform pair-authentication with the dock 100 over the wireless connection.

In an alternate embodiment, the authentication can occur between two interface devices operatively coupled to the server, such as when a physical dock 100 is unavailable with the medical care provider. Here, the server can be embodied as virtual docks which shall be registered, and each interface device shall be operatively coupled with a virtual dock 100 to enable secure transmission of information.

In another embodiment, a new interface device can be temporarily assigned a registration on request to allow transmission of information between the patient and an alternate medical care provider. The temporary registration can be initiated by the patient by means of any or a combination of biometric input, voice command, gesture command etc. In another embodiment, the alternate medical care provider shall also be required to be connected to the server by means of a log-in. The temporary registration is time-bound and can be modified by the patient. Further, any temporary registration and their modifications are stored on record.

In another embodiment, on successful authentication, an audio-video feed is made available between the patient and the medical care provider. The communication means as provided by the interface device is bonded with the communication from the dock 100 and is exchanged via the channels.

In another embodiment, the use of the second channel can require a third step of authentication and can be provided by the patient in the form of any or a combination of biometric input, voice command, gesture command etc.

In another embodiment, on successful authentication, the system can provide for the medical care provider to access historical data pertaining to the patient.

In another embodiment, on successful authentication, the system can further provide for remote operation by the medical care provider of the plurality of sensors coupled to the patient.

In another embodiment, the second and third steps of authentication can follow a similar procedure as for the first step of authentication including a verifications means being scanned by the camera on the HealthPOD upon request by the VA.

In another embodiment, the above described steps can be automatically performed by the interface device without involving the camera or the VA of the HealthPOD. Upon docking with the interface device, the HealthPOD start-up application can retrieve the WIFI credentials from the interface device. Once internet connectivity is accessed, the provisioning can be retrieved by the HealthPOD directly from the server.

It can be appreciated that the HealthPOD can be configured to have multiple steps of authentication as described above, or to have a single step of authentication that includes the multiple steps. It can also be appreciated that the system can be instrumented using different elements of the invention in a variety of configurations, which may range from a thin HealthPOD (with minimal functionality) together with a thick mobile application on the interface device on one extent to a thick HealthPOD (with maximum functionality) with a thin mobile application on the interface device on the other extent while the server functionality only differs in distribution of provisioning data, In another embodiment, the operation of the dock 100 and/or the connected interface device, including the authentication and instruction to transmit data can be through audio commands either locally or remotely.

In another embodiment, the system can comprise a third channel that is configured to connect a dock 100 with an emergency health care provider. The system is configured to recognise an emergency event for the patient based on monitoring of vital parameters associated with the health of the patient, through the plurality of sensors. On identification of the emergency event, the system, via the third channel, can be configured to contact the emergency medical care provider. The third channel can include transmission of data pertaining to the location of the patient, data pertaining to the emergency event and any other data deemed relevant to care that is required to be provided by the emergency medical care provider. In an exemplary embodiment, the third channel can be a dedicated channel for emergency healthcare. The system can be configured to continuously attempt connecting with the emergency medical care provider until the connection is successful.

In an exemplary embodiment, the apparatus and system can be configured for mobile use of the dock 100. The dock 100 can be taken to a remote location for providing medical opinions through secure channels. The use of easily available communications devices such as tablets and smart phones, coupled with the compact form factor of the dock 100 can enable the aforementioned mobility. Further, the dock 100 can be configured with a battery of a suitable energy density to power it.

In another exemplary embodiment, the apparatus and system can be configurable with a scope of additional and changed hardware on the dock 100 to suit different operations and with changes in the system to suit the different operations. It can be appreciated that the system can be instrumented using different elements of the invention in a variety of configurations, which may range from a thin HealthPOD (with minimal functionality) together with a thick mobile application on the interface device on one extent to a thick HealthPOD (with maximum functionality) with a thin mobile application on the interface device on the other extent while the server functionality only differs in distribution of provisioning data, In an exemplary implementation, the system can be configured to communicate with multiple registered docks simultaneously, such as between one patient and one or more medical care providers. However, as previously stated, the patient can control the flow of information from the end of the patient to the health care providers. Secure information can be transmitted to any or all the docks in simultaneous communication, on issuance of instruction from the patient.

In another exemplary implementation, the server can be configured to recognise instances when transmission of secure information can be allowed, and the server can be configured to allow flow of said secure information autonomously without explicitly requesting re-authorisation from the patient.

In another exemplary embodiment, the server can be configured with an Artificial Intelligence (AI) inference engine or interfaced with an external AI inference engine to process the patient vital sign data and the data related to the activities of daily living that are received from the patient's HealthPOD/interface device system in order to infer various health and behavioural patterns and provide AI-based patient diagnostics and the treatment.

The following section describes an instance of working of the system for remote health applications of the present disclosure. Once the HealthPOD and the interface device are bonded authenticated with the PodNET, and the user profiles and the healthcare applications of the HealthPOD and the interface device is synchronised, the system is prepared for remote health applications services. As part of synchronisation, the HealthPOD and the interface device resolve application relevant contact information of the users involved in order to facilitate hands-free working of the system. Alternatively, upon start-up, if the HealthPOD is not configured with necessary healthcare related configuration or with the necessary contact information, the VA can recognize it and initiate an interactive session with the user to configure the configuration and/or contact information. This can be enabled using interaction between the user and a voice assistant incorporated in the HealthPOD or the interface device. A part of the profile can also include information pertaining to use or restriction on the use of information such that information exchanged is in a manner that is HIPAA compliant.

In another embodiment, the HealthPOD and the paired interface device can be customised in that a name (or nickname) can be assigned by a user to facilitate easy identification. The HealthPOD and the interface device system can be addressed using the nickname such that, upon recognition of the nickname, the HealthPOD and/or the interface device executes any command that follows the nickname. In another embodiment, the command can be an instruction to the interface device or its voice assistant to execute operations by the interface device. In another embodiment, the command can be an instruction to the interface device or its voice assistant to execute operations by the HealthPOD apparatus.

In another embodiment, the HealthPOD and/or the mobile application on the interface device can be designed so that it can be customised and personalised as required by the users. For instance, on the side of the patient, the VA of the HealthPOD/interface device can be designed to act as a personal helper to the patient and can be customised and personalised by assigning any nickname as per the liking of the patient. Further personalisation can include changing the language of the VA, changing the gender of the VA, changing the accent of the VA etc. The HealthPOD/interface device can be personalised such that the patient is afforded a sense of comfort and familiarity with the VA.

In another instance, on the side of the medical care provider, the VA of the HealthPOD and/or the mobile application on the interface device can be designed to act as a nurse and can be customised and personalised by assigning any nickname that can identify the HealthPOD/interface device of the medical care provider regardless of patient or a set of patients.

In another embodiment, the HealthPOD can be configured to execute commands as received from a user remotely. The remote user can use a similar nickname for the HealthPOD/interface device or can assign the HealthPOD/interface device a new nickname. For instance, a medical care provider can communicate with the HealthPOD/interface device of a patient using the nickname provided by the patient. The VA can be instructed by the medical care provider to provide guidance or to operate any equipment it is operatively coupled with, as required.

Figure 3:
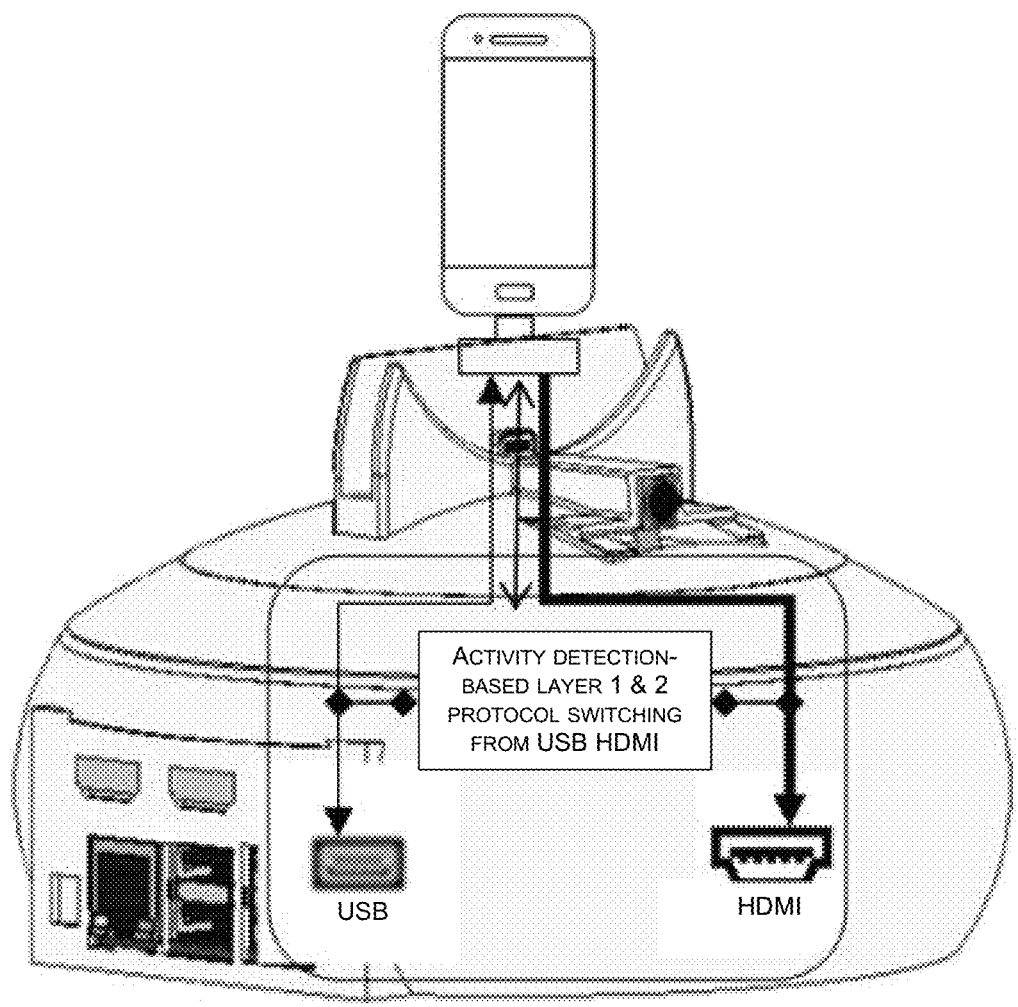
FIG. 3 illustrates an exemplary wired connectivity protocol between the dock and an interface device, in accordance with an embodiment of the present disclosure.

FIG. 3 illustrates an exemplary wired connectivity protocol between the dock 100 and an interface device, in accordance with an embodiment of the present disclosure. In an embodiment, the wired connectivity can be through simultaneous use of USB and HDMI technologies. In another embodiment, a USB connection can be established and maintained between the interface device and the dock 100. The USB connection can be a low data rate connection can be used for exchange of information that is required to comply with standard protocol such as a protocol determined by HIPAA. In an exemplary instance, the USB connection can be through a USB-C type interface or through its derivatives.

In another embodiment, simultaneous with the USB connection, a high data-rate HDMI connection can also be established between the interface device and the dock 100. High data rate functions such as audio-video communications can be exchanged using the HDMI connection, and the HIPAA compliant information can be exchanged through the low data rate USB connection. This enables simultaneous exchange of real-time audio-video data and real-time information to be compliant to HIPAA standards.

In an exemplary embodiment, the system can be configured to monitor exchange of HDMI data between the interface device and the dock 100 to determine low activity or frame repetition. Once a period of low activity is identified, the system can perform a prediction based deterministic bandwidth stealing to boost USB connectivity, while, at the same time, ensuring that HDMI connectivity is not degraded. For instance, for deterministic number of frame times of repetition, an example of low activity of the interface device is when display of interface device is idle or is showing the same frame.

Figure 4:
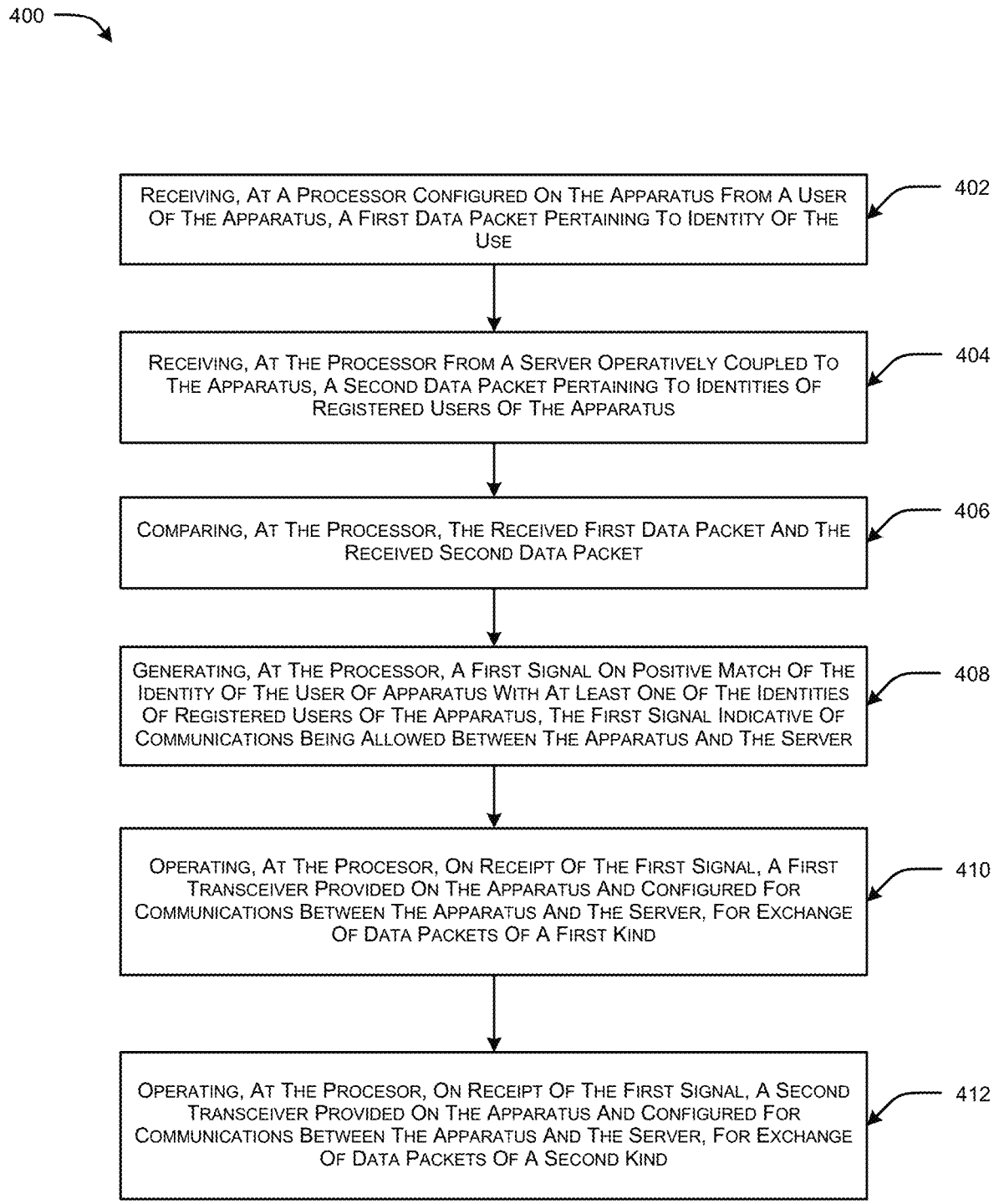
FIG. 4 illustrates an exemplary flow diagram for a method to operate the proposed apparatus for remote health monitoring, in accordance with an embodiment of the present disclosure.

FIG. 4 illustrates an exemplary flow diagram for a method to operate the proposed apparatus for remote health monitoring, in accordance with an embodiment of the present disclosure. The method 400 includes,

- 402—receiving, at a processor configured on the apparatus from a user of the apparatus, a first data packet pertaining to identity of the user;
- 404—receiving, at the processor from a server operatively coupled to the apparatus, a second data packet pertaining to identities of registered users of the apparatus;
- 406—comparing, at the processor, the received first data packet and the received second data packet;
- 408—generating, at the processor, a first signal on positive match of the identity of the user of apparatus with at least one of the identities of registered users of the apparatus, the first signal indicative of communications being allowed between the apparatus and the server;
- 410—operating, at the processor, on receipt of the first signal, a first transceiver provided on the apparatus and configured for communications between the apparatus and the server, for exchange of data packets of a first kind; and
- 412—operating, at the processor, on receipt of the first signal, a second transceiver provided on the apparatus and configured for communications between the apparatus and the server, for exchange of data packets of a second kind.

Figure 5:
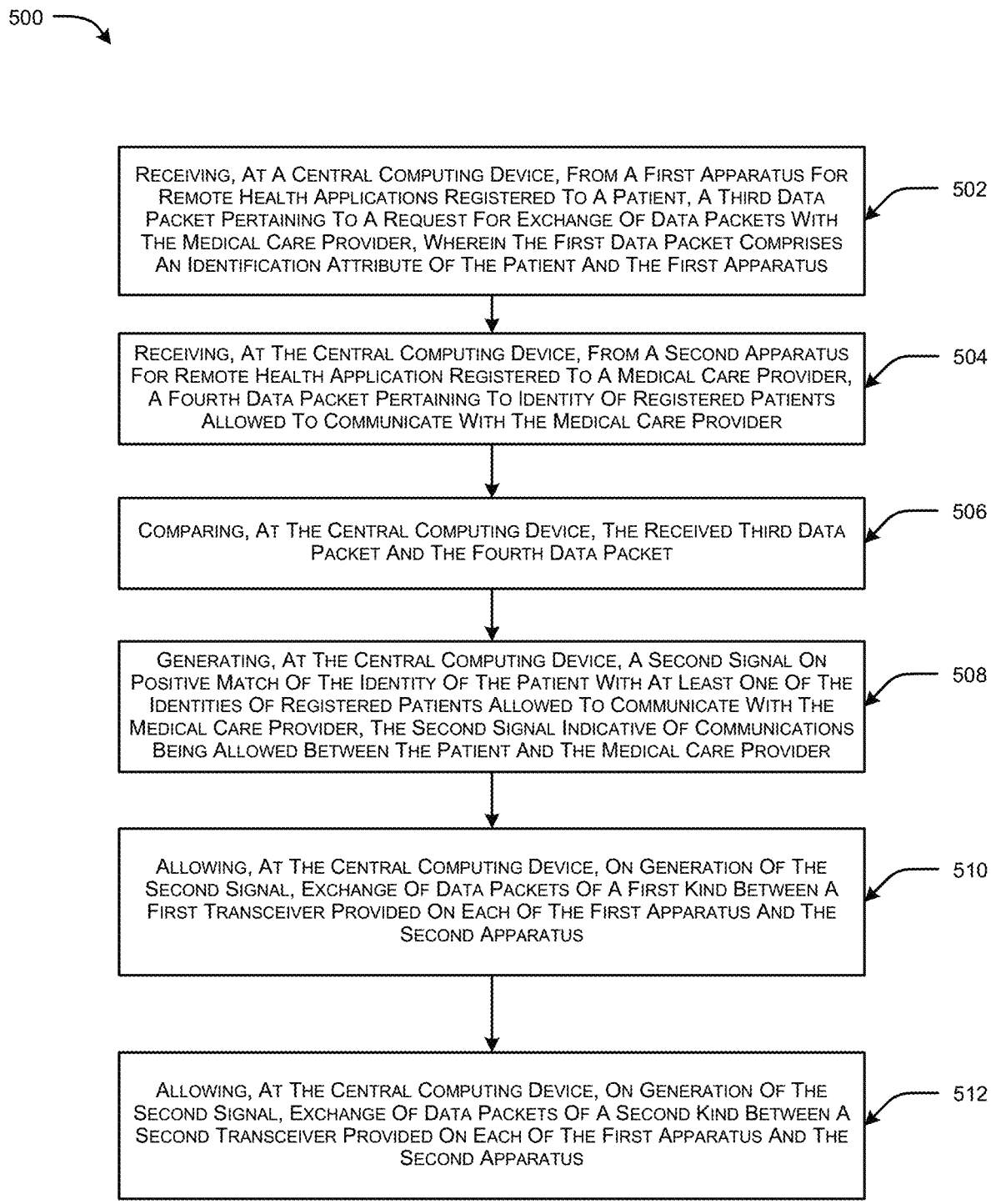
FIG. 5 illustrates an exemplary flow diagram for a method for remote health applications, in accordance with an embodiment of the present disclosure.

FIG. 5 illustrates an exemplary flow diagram for a method for remote health applications, in accordance with an embodiment of the present disclosure. The method 500 includes,

- 502—receiving, at a central computing device, from a first apparatus for remote health applications registered to a user (also, referred to as patient, herein), a third data packet pertaining to a request for exchange of data packets with the medical care provider, wherein the first data packet comprises an identification attribute of the patient and the first apparatus;
- 504—receiving, at the central computing device, from a second apparatus for remote health application registered to a medical care provider, a fourth data packet pertaining to identity of registered patients allowed to communicate with the medical care provider;
- 506—comparing, at the central computing device, the received third data packet and the fourth data packet;
- 508—generating, at the central computing device, a second signal on positive match of the identity of the patient with at least one of the identities of registered patients allowed to communicate with the medical care provider, the second signal indicative of communications being allowed between the patient and the medical care provider;
- 510—allowing, at the central computing device, on generation of the second signal, exchange of data packets of a first kind between a first transceiver provided on each of the first apparatus and the second apparatus; and
- 512—allowing, at the central computing device, on generation of the second signal, exchange of data packets of a second kind between a second transceiver provided on each of the first apparatus and the second apparatus.

Figure 6:
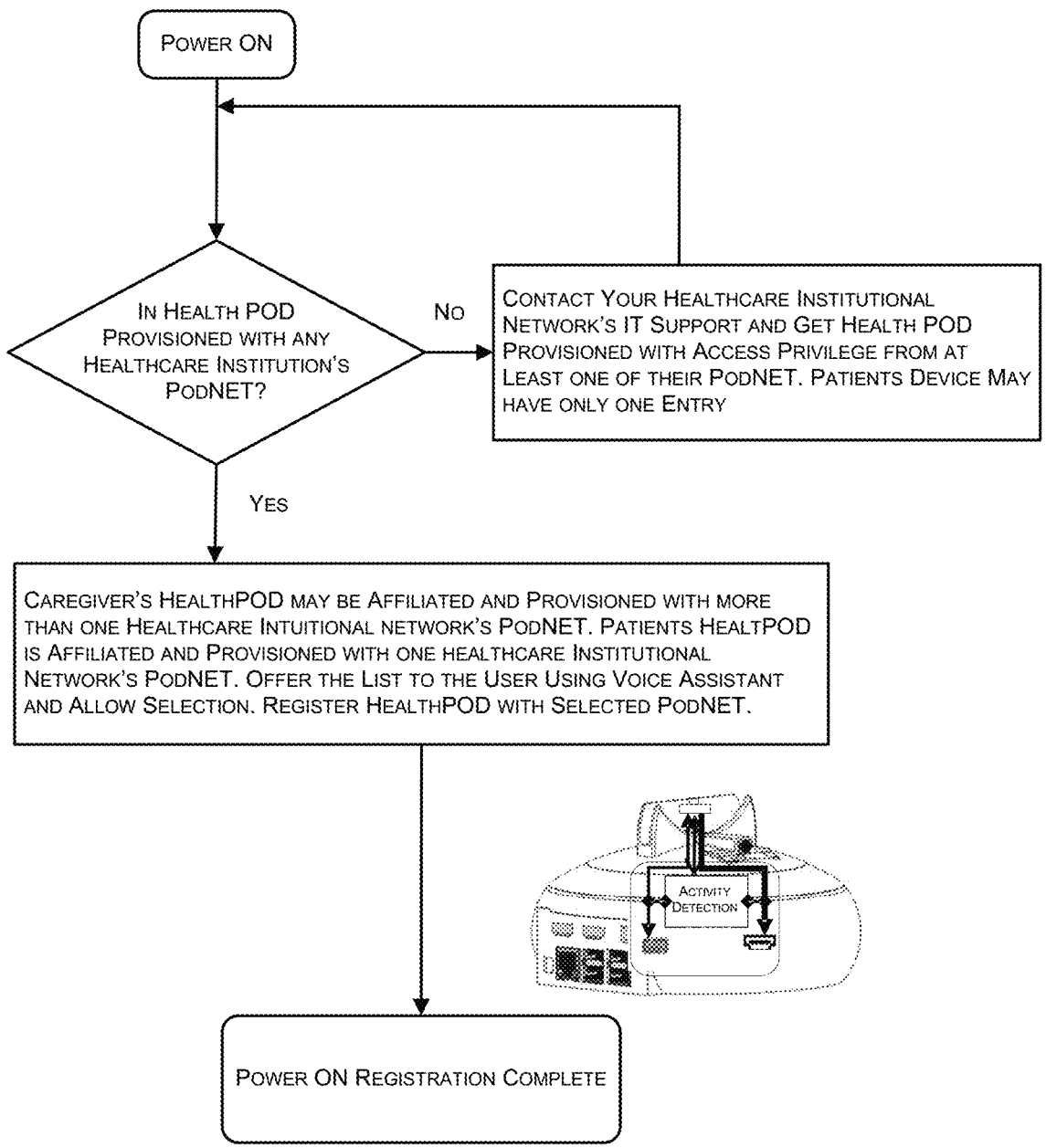
FIG. 6 illustrates an exemplary flow diagram for the process of registration of the dock, in accordance with an embodiment of the present disclosure.

FIG. 6 illustrates an exemplary flow diagram for the process of registration of the dock 100, in accordance with an embodiment of the present disclosure. In an embodiment, on being powered on, the dock 100 can be configured to initially check if it is provisioned by checking provisioning data. In an instance where the dock 100 is not provisioned, the dock 100 can prompt a user of the dock 100 to initiate provisioning process for the dock 100. In an implementation, the prompt from the dock 100 can be an interactive display or an audio-visual guide.

In another embodiment, procedure for provisioning can be based on minimalist embedded rules such as factory programming. The factory provisioning can be such as to enable the dock 100 to support different business models and their respective distribution channels through which the dock 100 can be sold to end-users. Some instances of factory programming can include, without limitation,

- an independent telemedicine healthcare brokering network to which individual healthcare networks and provider networks can be subscribed to, as well as to which healthcare service consumers can be subscribed to.
- any specific medical care provider network.
- any health insurance provider to which individual medical care providers are affiliated to as well as to which healthcare service consumers can subscribe to.
- any independent company offering remote medical assistance by leveraging smart devices from an end-user.
- any independent company offering medical assistance by enabling a medical care provider to provide a consultation at a patient site.
- any service network offering home care assistance to patients that the medical care provider network can be associated or affiliated with. The home care assistance can provide on-demand skills ranging from paramedical assistance to non-medical assistance.

In another embodiment, the dock 100 can allow trust to be established between a user and a networked member healthcare organisation. The trust can be established in the form of created trusted credentials between the dock 100 and the server. The credentials can be stored permanently and can be recalled whenever the dock 100 is powered on.

In another embodiment, once the dock 100 is provisioned, the dock 100 can prompt the user to register the dock 100 by selecting the preferred healthcare organisation and providing authenticating information. The authenticating information can be created at a first instance of registration and can be required to be provided at every subsequent access to the network. In another embodiment, the server can be configured to remember the authentication data. Once the dock 100 is registered, the dock 100 and an interface device can be paired.

Figure 7:
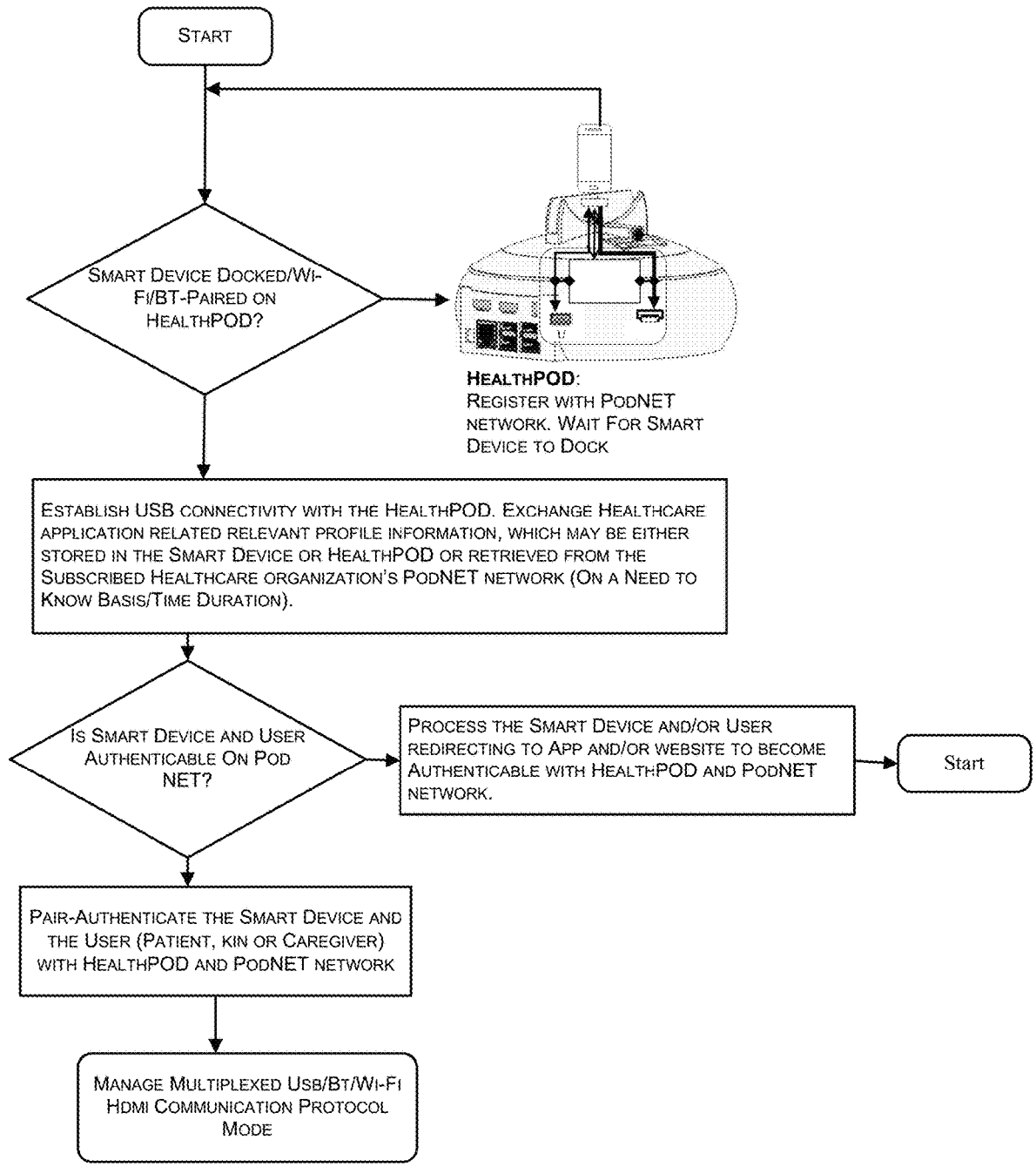
FIG. 7 illustrates an exemplary flow diagram for the process of docking of the interface device and its authentication, in accordance with an embodiment of the present disclosure.

FIG. 7 illustrates an exemplary flow diagram for the process of docking of the interface device and its authentication, in accordance with an embodiment of the present disclosure. In an embodiment, pairing of the interface device and the dock 100 can be through wired means or wireless means. The wired means can include wired internet, WAN internet etc., and the wireless means include Bluetooth, Wi-Fi etc. In another embodiment, when an interface device is physically paired with the dock 100, it can imply that the user of the interface device or the dock 100 intends to use the interface and the dock 100 for the purpose of remote healthcare monitoring. In order for that to happen, the dock 100 is to be registered and authenticated at the portal ("PodNET").

In another embodiment, a similar protocol as described above can be followed for pairing of the interface device by wireless means.

In an exemplary embodiment, where the interface device and the dock 100 are physically coupled, connectivity between the two is established via the USB and HDMI connections. Once connection is established, it is checked if registration and authentication of the dock 100 is complete.

If not, the user can be prompted to complete the steps of registration and authentication before proceeding further.

Figure 8A:
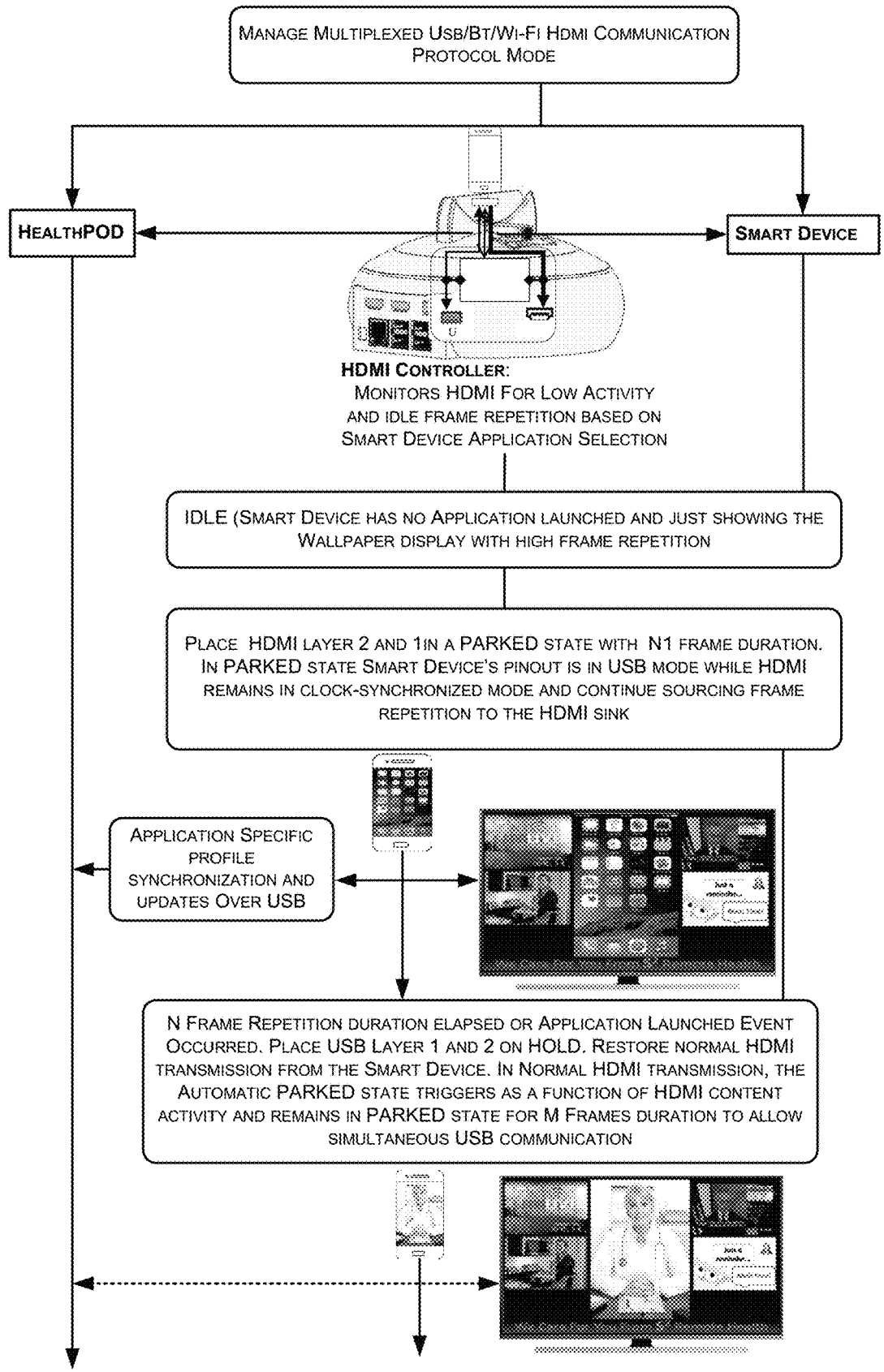
FIGS. 8A and 8B illustrate exemplary flow diagrams for the process of simultaneous USB and HDMI communication, in accordance with an embodiment of the present disclosure.
Figure 8B:
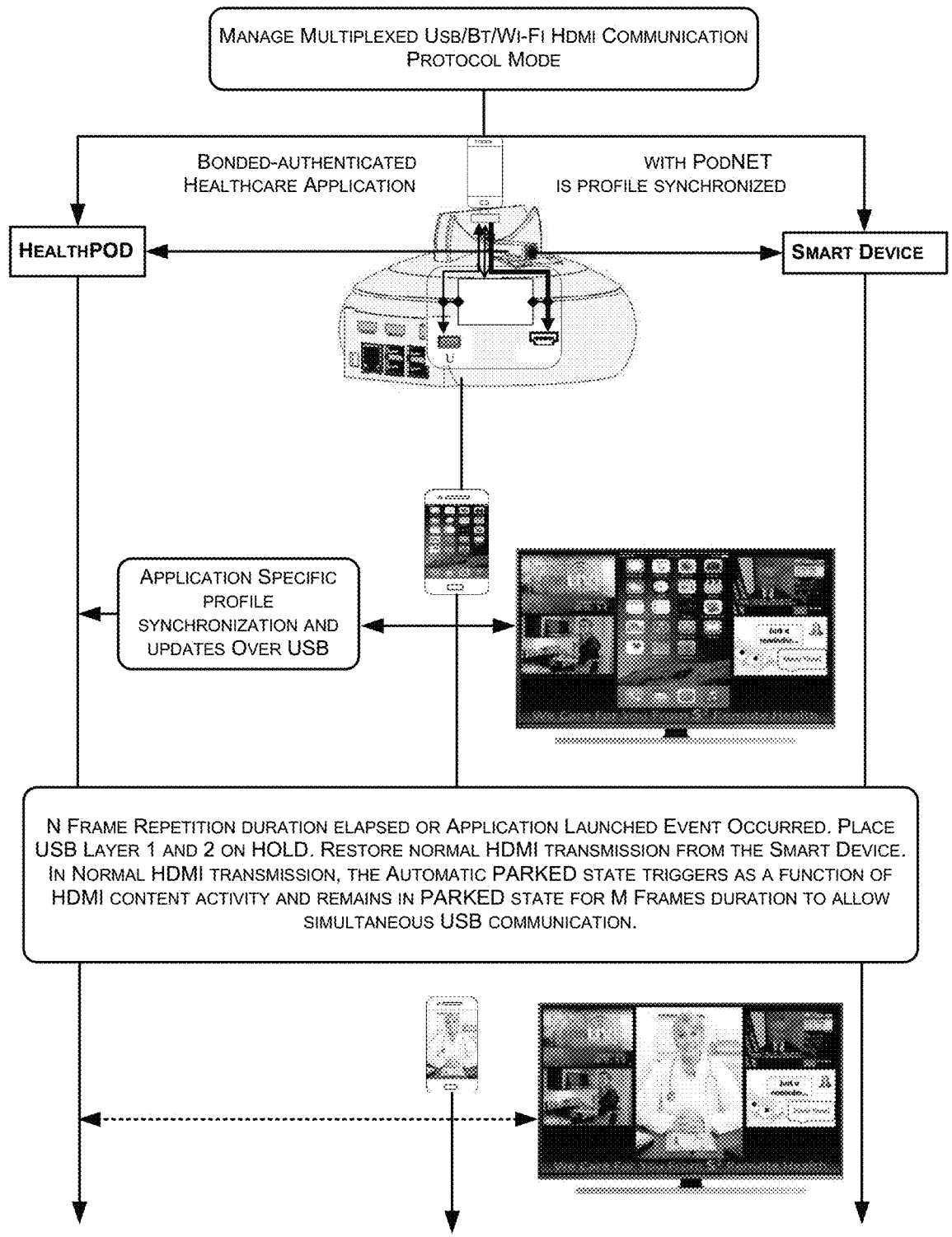

FIGS. 8A and 8B illustrate exemplary flow diagrams for the process of simultaneous USB and HDMI communication, in accordance with an embodiment of the present disclosure. In an embodiment, once the interface device and the dock 100 are registered and authenticated, they are pair and bonded authenticated on the PodNET and are ready for remote health applications. Based on rate of exchange of data and the type of data exchange, a USB, HDMI, or a combination of both can be a preferred mode of connection.

It can be appreciated by those versed in the art that the apparatus and system described herein are illustrations of an embodiment of the present disclosure and that they may not be construed as limitations to the scope of the present disclosure.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

Advantages of the Disclosure

The present disclosure provides an apparatus for remote health applications that is compliant to the Health Insurance Portability and Accountability Act (HIPAA).

The present disclosure provides an apparatus for remote health applications that can interface with available mobile devices.

The present disclosure provides a system for remote health applications that allows for remote diagnosis and remote prescriptions.

The present disclosure provides a system that provides remote monitoring of health of patients and allows alerts to be raised remotely.

We claim:

1. An apparatus for facilitating exchange of medical data pertaining to a user, comprising:
one or more processors operatively coupled with a memory, the memory storing instructions executable by the one or more processors to:
receive, from the user of the apparatus, a first data packet pertaining to identity of the user;
receive, from a server operatively coupled to the apparatus, a second data packet pertaining to identities of registered users of the apparatus; and
compare the received first data packet and the received second data packet,
wherein, the one or more processors are configured to generate a first signal on positive match of the identity of the user of apparatus with at least one of the identities of registered users of the apparatus, the first signal indicative of communications being allowed between the apparatus and the server, and
wherein the apparatus comprises:
a first transceiver configured for communications between the apparatus and the server, operable by the one or more processors, on receipt of the first signal, for exchange of data packets of a first kind, and
a second transceiver configured for communications between the apparatus and the server, operable by the one or more processors, on receipt of the first signal for exchange of data packets of a second kind.

2. The apparatus as claimed in claim 1, wherein the apparatus is configured to register a user to itself on initialisation of the apparatus, wherein the one or more processors are configured to:
operatively couple, upon initialisation of the apparatus, with the server;
receive, from an initially unregistered user, a request for registration of the apparatus, the request comprising identity attributes of the user, identity attributes of the apparatus and purpose of use of apparatus;
receive, from the initially unregistered user, an address of the user for communication of information from the server to the user;
request generation of a registration data packet at the server, comprising a registration parameter;
request transmission of the registration packet from the server to the address of the user;
request the initially unregistered user to input the registration parameter value into the apparatus; and
compare the input parameter value with the parameter value of the generated registration data packet,
wherein the one or more processors, upon positive match of the input parameter value and the parameter value of the registration data packet, are configured to register the initially unregistered user as a newly registered user of the apparatus; and
transmit information pertaining to the newly registered user of the apparatus to the server.

3. The apparatus as claimed in claim 1, wherein the apparatus is operatively coupled with one or more input devices, the input devices configured for exchange of information pertaining to health attributes of the user of the device, wherein the input devices are any or a combination of camera, microphone, implanted sensors and explanted sensors, and wherein the apparatus is operatively coupled to the input devices by any or a combination of wired and wireless means.

4. The apparatus as claimed in claim 3, wherein the apparatus comprises one or more one or more ports adapted for wired coupling between the apparatus and the input devices.

5. The apparatus as claimed in claim 1, wherein the apparatus is provided with a battery adapted to power the apparatus.

6. The apparatus as claimed in claim 1, wherein the apparatus is provided with an interface device operatively coupled to it, and wherein the one or more processors of the apparatus is configured to operate the an interface device to facilitate communications between the user and the apparatus.

7. The apparatus as claimed in claim 6, wherein the apparatus comprises a movable receptacle fixed at a top surface of the apparatus, the receptacle adapted to hold, rotate and tilt the interface device within a pre-defined range.

8. The apparatus as claimed in claim 6, wherein the apparatus is operable in any or a combination of tilt mode and pan mode;
wherein the tilt mode facilitates tilting of the interface device in order to track the user; and the pan mode facilitates panning, through the interface device, to obtain a clear view of the user.

9. The apparatus as claimed in claim 8, wherein the apparatus facilitates a user to select, through any of an input device and the interface device, any or a combination of the tilt mode and pan mode, to operate the interface device.

10. The apparatus as claimed in claim 8, wherein the apparatus comprises implanted sensors configured to sense motion of the user, and wherein in response to the sensed motion, any or a combination of the tilt mode and pan mode is automatically selected.

11. The apparatus as claimed in claim 1, wherein the apparatus is provided with an interactive voice assistant to facilitate communications between the apparatus and the user through an interface device of the user.

12. The apparatus as claimed in claim 1, wherein the data packets of the first kind pertain to information pertaining to the user that is not protected by a security protocol.

13. The apparatus as claimed in claim 1, wherein the data packets of the second kind pertain to information pertaining to the user that is protected by security protocol, and wherein the security protocol is Health Insurance Portability and Accountability Act (HIPAA).

14. A method to operate an apparatus for facilitating exchange of medical data pertaining to a user, comprising:
 receiving, at a processor configured on the apparatus from the user of the apparatus, a first data packet pertaining to identity of the user;
 receiving, at the processor from a server operatively coupled to the apparatus, a second data packet pertaining to identities of registered users of the apparatus;
 comparing, at the processor, the received first data packet and the received second data packet; and
 generating, at the processor, a first signal on positive match of the identity of the user of apparatus with at least one of the identities of registered users of the apparatus, the first signal indicative of communications being allowed between the apparatus and the server,
wherein, on generation of the first signal, a first transceiver provided on the apparatus and configured for communications between the apparatus and the server is operable by the processor for exchange of data packets of a first kind, and wherein, on generation of the first signal, a second transceiver provided on the apparatus and configured for communications between the apparatus and the server is operable by the processor for exchange of data packets of a second kind.

15. A system for facilitating exchange of medical data pertaining to a user, comprising:
 a first apparatus for remote health monitoring registered to the user;
 a second apparatus for remote health monitoring registered to a medical care provider; and
 a server operatively coupled with the first apparatus and the second apparatus, comprising one or more processors operatively coupled with a memory, the memory storing instructions executable by the one or more processors to:
  receive, from the first apparatus, a third data packet pertaining to a request for exchange of data packets with the medical care provider, wherein the first data packet comprises an identification attribute of the user and the first apparatus;
  receive, from a second apparatus for remote health application, a fourth data packet pertaining to identity of registered users allowed to communicate with the medical care provider;
  compare the received third data packet and the fourth data packet,
 wherein, the one or more processors is configured to generate a second signal on positive match of the identity of the user with at least one of the identities of registered users allowed to communicate with the medical care provider, the second signal indicative of communications being allowed between the user and the medical care provider,
 wherein the one or more processors are configured to allow exchange of data packets of a first kind between a first transceiver provided on each of the first apparatus and the second apparatus, and
 wherein the one or more processors are configured to allow exchange of data packets of a second kind between a second transceiver provided on each of the first apparatus and the second apparatus.

16. The system as claimed in claim 15, wherein the server is configured to register a user to an apparatus for remote health applications on initialisation of the apparatus,
 wherein the one or more processors are configured to:
  receive, from an initially unregistered user, a request for registration of the apparatus to the user, the request comprising identity attributes of the user, identity attributes of the apparatus and purpose of use of apparatus by the user;
  receive, from the initially unregistered user, an address of the user for communication of information from the server to the user;
  generate a registration data packet comprising a registration parameter;
  transmit the registration packet to the address of the user;
  request, at the apparatus, the initially unregistered user to input the registration parameter value into the apparatus; and
  compare the input parameter value with the parameter value of the generated registration data packet,
 wherein the one or more processors, upon positive match of the input parameter value and the parameter value of the registration data packet, are configured to register the initially unregistered user as a newly registered user of the apparatus.

17. The system as claimed in claim 15, wherein the server is operatively coupled to any or both of the first apparatus and the second apparatus through a mobile computing device operatively coupled correspondingly with the first apparatus and the second apparatus.

18. The system as claimed in claim 15, wherein the data packets of the first kind pertain to information pertaining to the user that is not protected by a security protocol.

19. The system as claimed in claim 15, wherein the data packets of the second kind pertain to information pertaining to the user that is protected by security protocol, and wherein the security protocol is Health Insurance Portability and Accountability Act (HIPAA).

20. A method for facilitating exchange of medical data pertaining to a user, comprising:
 receiving, at a central computing device, from a first apparatus for remote health applications registered to the user, a third data packet pertaining to a request for exchange of data packets with the medical care provider, wherein the first data packet comprises an identification attribute of the user and the first apparatus;
 receiving, at the central computing device, from a second apparatus for remote health application registered to a medical care provider, a fourth data packet pertaining to identity of registered users allowed to communicate with the medical care provider;
 comparing, at the central computing device, the received third data packet and the fourth data packet;
 generating, at the central computing device, a second signal on positive match of the identity of the user with at least one of the identities of registered users allowed to communicate with the medical care provider, the second signal indicative of communications being allowed between the user and the medical care provider, wherein, on generation of the second signal, the central computing device is configured to allow exchange of data packets of a first kind between a first transceiver provided on each of the first apparatus and the second apparatus, and wherein, on generation of the second signal, the central computing device is configured to allow exchange of data packets of a second kind between a second transceiver provided on each of the first apparatus and the second apparatus.

\* \* \* \* \*